Figure 1:
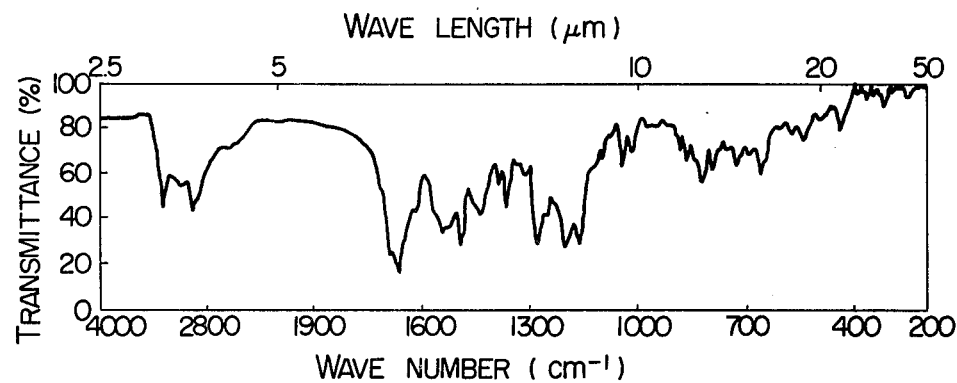

United States Patent [19]

Nagasawa et al.

[11] 4,209,459
[45] Jun. 24, 1980

[54] NOVEL L-LEUCYL-4-HYDROXYANILIDE DERIVATIVES

[75] Inventors: Takeshi Nagasawa; Katsumasa Kuroiwa, both of Koriyama; Tadami Akatsuka, Tsuchiura; Osamu Kodama, Ibaraki; Mitoshi Shimamoto, Funabashi, all of Japan

[73] Assignees: Nitto Boseki Co., Ltd., Fukushima; Iatron Laboratories, Inc., Tokyo, both of Japan

[21] Appl. No.: 36,094

[22] Filed: May 4, 1979

[30] Foreign Application Priority Data

Jun. 1, 1978 [JP] Japan .................................. 53/66274

[51] Int. Cl.$^2$ .................. C07C 143/44; C07C 101/72
[52] U.S. Cl. .............................. 260/507 R; 435/212; 562/451; 435/24
[58] Field of Search ..................... 260/507 R; 562/451

[56] References Cited

U.S. PATENT DOCUMENTS

| 3,340,298 | 9/1967 | Wismayr et al. ................... 562/451 |
| 4,049,702 | 9/1977 | Bernt et al. ...................... 260/507 R |

*Primary Examiner*—Nicky Chan
*Attorney, Agent, or Firm*—Norbert P. Holler

[57] ABSTRACT

Novel L-leucyl-4-hydroxyanilide derivatives of the formula,

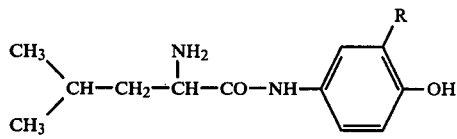

wherein R represents a carboxyl group or a sulfo group or an acid addition salt thereof, which are useful for assay of leucine-aminopeptidase activity.

3 Claims, 3 Drawing Figures

NOVEL L-LEUCYL-4-HYDROXYANILIDE DERIVATIVES

This invention relates to novel L-leucyl-4-hydroxyanilide derivatives, a method for the assay of leucine-aminopeptidase activity by using said anilide derivatives and a method for the preparation of said anilide derivatives.

As known well, leucine-aminopeptidase (hereinafter referred to as LAP) is an enzyme capable of liberating leucine from L-peptides, particularly those peptide compounds having amino-terminal leucine groups. This enzyme is widely distributed in living tissues and exists also in sera. The LAP content of a serum has been known to vary markedly with the condition of the living body from which the serum has been derived. The LAP activity increases in the serum of a patient suffering from acute hepatitis, hepatoma, metastatic hepatoma, liver cirrhosis, or cholangia. Accordingly, the LAP activity became one of the indications of the above-noted diseases and the assay of the LAP activity has become one of the indispensable tests for the dignosis of these diseases.

For the assay of LAP activity, there were proposed several methods, in most of which amine compounds liberated from synthetic substrates formed by the action of LAP are colorimetrically determined.

However, since all of these methods revealed merits and demerits, development of a new synthetic substrate has been awaited. For instance, the L-leucyl-$\beta$-naphthylamide method [Cancer, Vol. 11, 283 (1958)] requires $\beta$-napthylamine as the standard substance. Because of its carcinogenicity, $\beta$-naphthylamine is one of the substances of which the commercial production has been prohibited and in using $\beta$-naphthylamine it is necessary to wear protective outfits and to take utmost care. The influence of serum ingredients is unavoidable in a method in which L-leucyl-p-nitroanilide is used as the substrate and yellow p-nitroaniline which is formed is colorimetrically determined [Klin. Wochenschr., Vol. 45, 474 (1967)]. The colorimetric determination of p-nitroaniline after condensation with dimethylaminocinnamaldehyde is undesirable in the reproducibility, because the color development is too sensible to the change in temperature. Recently, an attempt was made to assay the LAP activity by using a L-leucyl-p-aminoanilide derivative as the substrate and determining colorimetrically the formed p-aminoanilide derivative after oxidative condensation with a suitable coupler [Japanese Patent Application Laid-open ("Kokai") 52,691/77]. This method has disadvantages in that the substrate reactivity is comparable or somewhat inferior to that of L-leucyl-$\beta$-naphthylamide and the method gives too high an activity value when applied to the serum of a pregnant woman.

An object of this invention is to provide a substrate for use in the assay of LAP activity, which has sufficient solubility in water and properties capable of overcoming the difficulties encountered by the prior art in safety, reproducibility, stability, reactivity and selectivity.

Another object of this invention is to provide a method for assaying the LAP activity, which comprises the use of the said substrate.

Furthermore, to provide a method for producing said substrate is also one of the objects of this invention.

The present inventors conducted studies on the improvement of conventional methods for the assay of LAP activity which have aforementioned disadvantages. As a result, they found a novel substrate having excellent properties. This finding has led to the accomplishment of this invention.

This invention relates to an L-leucyl-4-hydroxyanilide derivative represented by the formula,

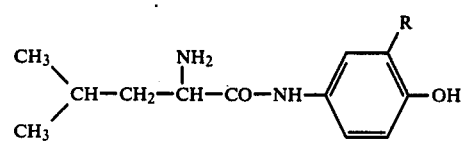

or an acid addition salt thereof which is useful as the substrate in assaying the LAP activity. In the above formula, R represents a carboxyl or sulfo group.

As described hereunder, the compound of this invention is an excellent substrate which shows none of the aforementioned disadvantages of the conventional substrates used in assaying the LAP activity.

The compound of this invention is sufficiently soluble in water and has a substrate reactivity toward LAP twice or more as high as that of any conventional substrate, as shown in Table 1.

Table 1

| Substrate | Relative substrate reactivity |
|---|---|
| Substrate reactivity | |
| Conventional substrate: | |
| L-leucyl-$\beta$-naphthylamide | 100 |
| L-leucyl-4-N,N-diethylaminoanilide | 81 |
| L-leucyl-p-nitroanilide | 95 |
| Substrate of this invention: | |
| L-leucyl-3-carboxy-4-hydroxyanilide | 223 |
| L-leucyl-3-sulfo-4-hydroxyanilide | 263 |

The above-noted properties suggest the advantages of the substrate of this invention, such as easy preparation of reagents, reduction in the time required for the assay, reduction in the quantity of sample necessary for the measurement, etc.

As mentioned afore, the use of the compound is in the assay of LAP activity. In performing the assay, the substrate of this invention is allowed to react with LAP of a serum in a buffer solution of pH 6.5 to 7.5 and the 4-hydroxyanilide derivative formed by the reaction is allowed to undergo oxidative condensation with a suitable coupler to form a colored substance which is then determined by colorimetry to assay the LAP activity of the serum.

Suitable couplers for the development of color in acidic side are aniline compounds such as, for example, N,N-diethylaniline and those for the development of color in the alkaline side are phenol and naphthol compounds such as, for example, m-cresol.

The oxidizing agent most suitable for use in the above oxidative condensation is sodium metaperiodate, though various others such as hydrogen peroxide, persulfates and the like can be used.

The colored substance formed by the oxidative condensation between a coupler and the product of reaction between LAP and the compound of this invention shows a maximum absorption in a brood wave length range of from 560 to 770 nm depending on the type of coupler. The color development is affected very little by the change in reaction temperature and time and is sufficiently steady to meet the most important requirement for the reagent used in such a type of assay.

The colorimetry in the conventional methods is conducted at a wave length shorter than 560 nm, whereas the colorimetry in the method of this invention is conducted at a wave length longer than 560 nm. Therefore, the colorimetry in the method of this invention is scarcely affected by the presence of impurities in the serum and, hence, a blank test for each sample is not necessary, resulting in saving of labor and time.

Further, in conventional methods, it was difficult to eliminate the adverse effect of reducing substances in serum, such as uric acid and ascorbic acid, whereas in the method of this invention, the effect of such reducing substances on the accuracy of measurement is very little, because these reducing substances are decomposed by the oxidizing agent existing in excess.

From the foregoing description, it is apparent that as a substrate for the assay of LAP activity, the compound of this invention is far superior to the conventional ones.

The novel compound of this invention can be prepared in a customary way by allowing an activated L-leucine having its amino group protected to react with a p-hydroxyaniline derivative and then removing the protective group from the leucyl-4-hydroxyanilide derivative formed by the reaction.

Examples of activated L-leucine for use as starting material include activated esters represented by the formula, $$X-NH-CHC-Y$$
$$\quad\quad\quad |$$
$$\quad\quad\quad CH_2$$
$$\quad\quad\quad |$$
$$\quad\quad\quad CH$$
$$\quad\quad\quad / \backslash$$
$$\quad\quad CH_3 \quad CH_3$$

(with C=O on the CHC)

wherein X represents a N-protective group such as tertbutyloxycarbonyl, p-methoxybenzyloxycarbonyl, benzyloxycarbonyl or phthalyl and Y represents an activating group such as

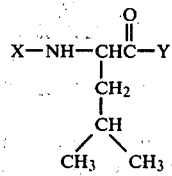

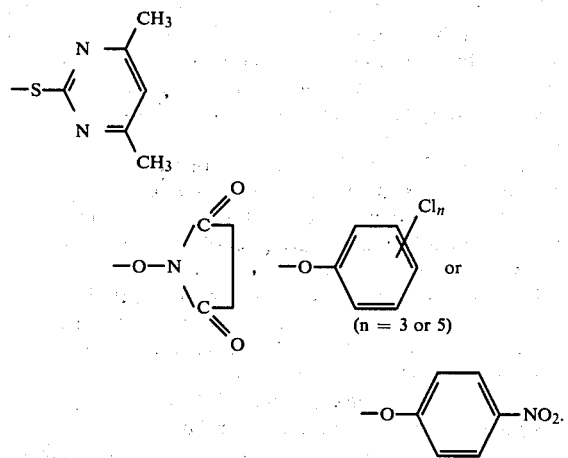

The liberated compound (HY) is preferably

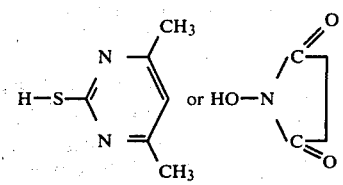

which is soluble in water or an acidic aqueous solution.

The removal of the protective group can be effected in a known way.

The reaction is carried out in an organic solvent and generally in the presence of an amine. Suitable organic solvents include tetrahydrofuran, dimethylformamide, dioxane and ethyl acetate. Suitable amines are tertiary amines such as triethylamine, N-methylmorpholine and N-ethylmorpholine. "Triton B" (benzyltrimethyl ammonium hydroxide) can also be used.

The preparative procedure is illustrated below in detail with reference to Examples, but the invention is not limited to the Examples.

EXAMPLE 1

Preparation of L-leucyl-3-carboxy-4-hydroxyanilide hydrochloride.

In 100 ml of dimethylformamide, were dissolved 7.7 g (0.05 mole) of 5-aminosalicyclic acid and 14 ml (0.10 mole) of triethylamine. To the solution was added dropwise over one hour at $-5°$ to $0°$ C. a solution of 17.3 g (0.05 mole) of tert-butyloxycarbonyl-L-leucyl-4,6-dimethylpyrimidin-2-yl thioester in 150 ml of tetrahydrofuran. While stirring at room temperature, the mixture was allowed to react for further 18 hours. The reaction mixture was then distilled to remove the solvent. The residue was extracted with 300 ml of ethyl acetate. The ethyl acetate layer was washed successively with cold 5% hydrochloric acid, water and saturated aqueous sodium chloride solution, then decolored and dried over a magnesium sulfate-activated carbon mixture. The ethyl acetate layer thus treated was distilled to remove the ethyl acetate, leaving behind a crystalline substance. This substance was further recrystallized from an ethyl acetate-petroleum ether mixture to obtain 12.4 g (68%) of white crystals. Melting point: $168°-170°$ C.; specific rotation: $[\alpha]_D^{20} = -16.4$ (C=1, DMF). Elementary analysis: $C_{18}H_{26}N_2O_6$ (molecular weight 366.4)

|  | C % | H % | N % |
|---|---|---|---|
| Found: | 58.98 | 7.28 | 7.88 |
| Calculated: | 59.01 | 7.15 | 7.65 |

Thin layer chromatography:
Rf=0.39 (CHCl$_3$:MeOH:AcOH:H$_2$O = 80:20:2.5:5)

In 30 ml of a mixture of 2.4 N hydrochloric acid and acetic acid, was dissolved 10 g (0.027 mole) of the tert-butyloxycarbonyl-L-leucyl-3-carboxy-4-hydroxyanilide obtained above. The solution was allowed to react at room temperature for 2 hours to remove the tert-butyloxycarbonyl group. The reaction mixture was added to 500 ml of dried ether. The white precipitates which were formed were collected by filtration and dried to obtain quantitatively 8.3 g of intended L-leucyl-3-carboxy-4-hydroxyanilide hydrochloride. Melting point: $217°$ C. (decomp.); specific rotation:

$[\alpha]_D^{20} = +36.3$ (C=1, MeOH); Rf=0.70 (n-BuOH-:AcOH:H$_2$O=4:1:1). Elementary analysis: C$_{13}$H$_{19}$N$_2$O$_4$Cl.½H$_2$O (molecular weight 311.783)

|  | C % | H % | N % |
|---|---|---|---|
| Found: | 50.15 | 6.57 | 8.82 |
| Calculated: | 50.04 | 6.47 | 8.98 |

EXAMPLE 2

Preparation of L-leucyl-3-sulfo-4-hydroxyanilide.

To 200 ml of methanol, were added 7.6 g (40 millimoles) of 3-sulfo-4-hydroxyaniline and 18.4 ml (40% solution in methanol) of Triton B. The mixture was heated to form a homogeneous solution and then evaporated to remove the methanol. The residue was dissolved in 50 ml of dimethylformamide, admixed with 15.5 g (40 millimoles) of benzyloxycarbonyl-L-leucyl-4,6-dimethylpyrimidin-2-yl thioester and allowed to react at room temperature for 48 hours. After addition of 300 ml of ethyl acetate, the reaction mixture was successively washed each twice with 60 ml of cold 5 N hydrochloric acid, 60 ml of 2 N hydrochloric acid, and 60 ml of 5% hydrochloric acid saturated with sodium chloride. The ethyl acetate solution thus treated was dried over anhydrous magnesium sulfate and freed from the ethyl acetate by distillation to obtain benzyloxycarbonyl-L-leucyl-3-sulfo-4-hydroxyanilide as an oily residue. The oily residue was mixed with 47 ml of a mixture of 25% hydrobromic acid and acetic acid, allowed to react at room temperature for one hour, and then poured into 470 ml of ether. The precipitates which were formed were collected by filtration, washed with ethyl ether, and recrystallized from an ethyl alcohol-ethyl ether mixture to obtain 5.8 g (41%) of L-leucyl-3-sulfo-4-hydroxyanilide. Melting point: 214°–217° C.; specific rotation: $[\alpha]_D^{20} = +57.6$ (C=1, H$_2$O); Rf=0.52 (n-BuOH:AcOH:H$_2$O=4:1:1). Elementary analysis: C$_{12}$H$_{18}$N$_2$O$_5$S.3/7HBr. H$_2$O (molecular weight 355.417)

|  | C % | H % | N % | S % | Br % |
|---|---|---|---|---|---|
| Found: | 40.41 | 5.68 | 7.86 | 9.11 | 9.42 |
| Calculated: | 40.55 | 5.79 | 7.88 | 9.02 | 9.42 |

Figure 2:
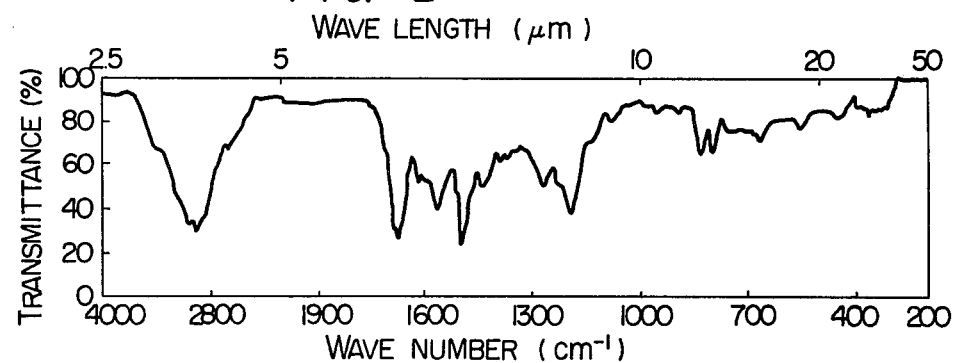
Figure 3:
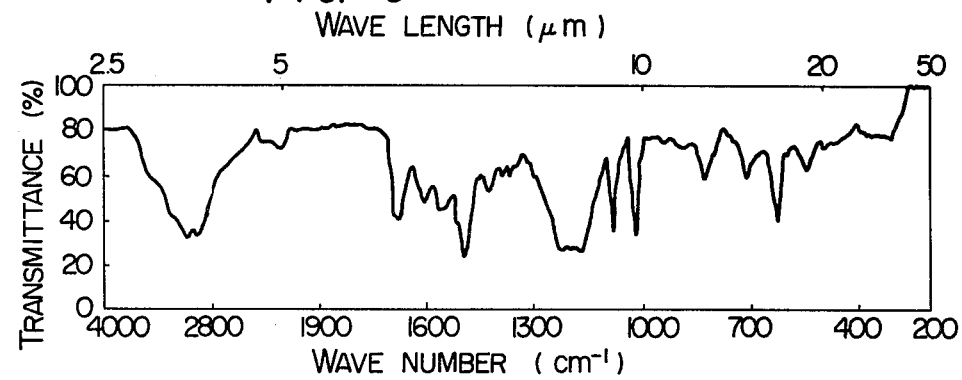

FIG. 1, FIG. 2 and FIG. 3 are infrared absorption spectra of tert-butyloxycarbonyl-L-leucyl-3-carboxy-4-hydroxyanilide, L-leucyl-3-carboxy-4-hydroxyanilide hydrochloride, and L-leucyl-3-sulfo-4-hydroxyanilide, respectively.

What is claimed is:

1. An L-leucyl-4-hydroxyanilide derivative represented by the general formula,

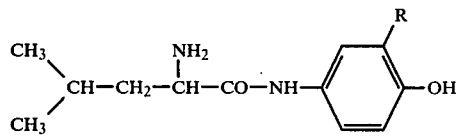

(wherein R represents a carboxyl group or a sulfo group) or an acid addition salt thereof.

2. A compound according to claim 1, wherein R is a carboxyl group.

3. A compound according to claim 1, wherein R is a sulfo group.

* * * * *